(12) United States Patent
Grundhoefer et al.

(10) Patent No.: US 12,688,924 B1
(45) Date of Patent: Jul. 21, 2026

(54) USER FEEDBACK DURING FOOD TRACKING

(71) Applicant: Apple Inc., Cupertino, CA (US)

(72) Inventors: Anselm Grundhoefer, Campbell, CA (US); Mohamed Selim Ben Himane, Palo Alto, CA (US); Shubham Agrawal, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 531 days.

(21) Appl. No.: 18/136,100

(22) Filed: Apr. 18, 2023

Related U.S. Application Data

(60) Provisional application No. 63/332,820, filed on Apr. 20, 2022.

(51) Int. Cl.
*G16H 20/60* (2018.01)
*G06F 3/01* (2006.01)
*G06T 19/00* (2011.01)

(52) U.S. Cl.
CPC ............ *G16H 20/60* (2018.01); *G06F 3/011* (2013.01); *G06T 19/006* (2013.01)

(58) Field of Classification Search
CPC ........ G16H 20/60; G06F 3/011; G06T 19/006
USPC .......................................................... 434/13
See application file for complete search history.

(56) References Cited

U.S. PATENT DOCUMENTS

| | | | | |
|---|---|---|---|---|
| 7,914,468 | B2 * | 3/2011 | Shalon | A61B 5/0006 |
| | | | | 600/595 |
| 9,529,385 | B2 | 12/2016 | Connor | |
| 9,659,225 | B2 | 5/2017 | Joshi et al. | |
| 9,734,426 | B2 | 8/2017 | Divakaran et al. | |
| 10,736,566 | B2 | 8/2020 | Sazonov et al. | |
| 10,901,509 | B2 | 1/2021 | Aimone et al. | |
| 11,594,315 | B2 | 2/2023 | Oh et al. | |
| 2014/0140570 | A1 | 5/2014 | Ross et al. | |

(Continued)

FOREIGN PATENT DOCUMENTS

| | | |
|---|---|---|
| CN | 114358163 A | 4/2022 |

OTHER PUBLICATIONS

U.S. Patent and Trademark Office, Non-Final Office Action, U.S. Appl. No. 18/136,024, 10 pages, Jun. 16, 2025.
Vu, Tri, Lin, Feng, Alshurafa, Nabil, and Xu Wenyao, "Wearable Food Intake Monitoring Technologies: A Comprehensive Review"; MDPI Computers; Jan. 24, 2017; pp. 1-28.
Liu, Jindong, Johns, Edward, Atallah, Louis, Pettitt, Claire, Lo, Benny, Frost, Gary and Yang, Guang-Zhong; "An Intelligent Food-intake Monitoring System Using Wearable Sensors"; The Hamlyn Centre, Imperial College London, UK; May 17, 2012; pp. 1-7.

(Continued)

*Primary Examiner* — Pierre E Elisca
(74) *Attorney, Agent, or Firm* — Thompson Hine LLP

(57) ABSTRACT

Various implementations disclosed herein use user input received approximately around the time of food consumption to confirm and/or revise food predictions, e.g., regarding type of food, volume, etc. One or more food characteristics determinations may be associated with uncertainty. User input is implicitly or explicitly requested to resolve at least some of such ambiguities and uncertainties approximately around the time of food consumption. The user feedback experience may be configured to be easy and unobtrusive by presenting limited options in limited circumstances and using easy and intuitive input mechanisms. As examples, such feedback may involve a user using gaze input, a voice command, or a hand gesture to quickly identify whether an uncertain item is of one type or another type, e.g., mashed potatoes or ice-cream. In some implementations, the obtrusiveness/burden of requiring live input for every food determination is avoided or reduced by only asking about some items.

20 Claims, 4 Drawing Sheets

(56) References Cited

U.S. PATENT DOCUMENTS

| | | | |
|---|---|---|---|
| 2014/0315160 A1 | 10/2014 | Hayashi et al. | |
| 2016/0232811 A9 | 8/2016 | Connor | |
| 2017/0270821 A1 | 9/2017 | Jerauld | |
| 2018/0053263 A1 | 2/2018 | Kumar et al. | |
| 2018/0242908 A1* | 8/2018 | Sazonov | A61B 5/4866 |
| 2019/0354926 A1 | 11/2019 | Im | |
| 2020/0013190 A1 | 1/2020 | Li et al. | |
| 2020/0020165 A1 | 1/2020 | Tran et al. | |
| 2020/0033179 A1 | 1/2020 | Gurumohan et al. | |
| 2020/0289055 A1 | 9/2020 | Vleugels | |
| 2021/0350920 A1* | 11/2021 | Vleugels | G16H 40/63 |
| 2021/0398645 A1 | 12/2021 | Dev et al. | |
| 2022/0415476 A1 | 12/2022 | Connor | |
| 2023/0191615 A1 | 6/2023 | Creusot et al. | |
| 2024/0177824 A1 | 5/2024 | Kim et al. | |

OTHER PUBLICATIONS

Field, Karen, "A Wearable device that tracks how much you eat"; Sep. 10, 2020, pp. 1-4.

Jiang, Haotian, Starkman, James, Liu, Menghan and Huang, Ming-Chun; IEEE Consumer Electronics Magazine, "Food Nutrition Visualization on Google Glass", Apr. 10, 2018; pp. 21-31.

USPTO, Interview Summary issued in U.S. Appl. No. 18/136,004 dated Nov. 21, 2025 (Two pages).

USPTO, Final Rejection issued in U.S. Appl. No. 18/136,024 dated Nov. 28, 2025 (12 pages).

USPTO, Non-Final Offce Action issued in U.S. Appl. No. 18/136,004 dated Jul. 30, 2025 (26 pages).

USPTO, Interview Summary issued in U.S. Appl. No. 18/136,024 dated Sep. 16, 2025 (Two pages).

* cited by examiner

700

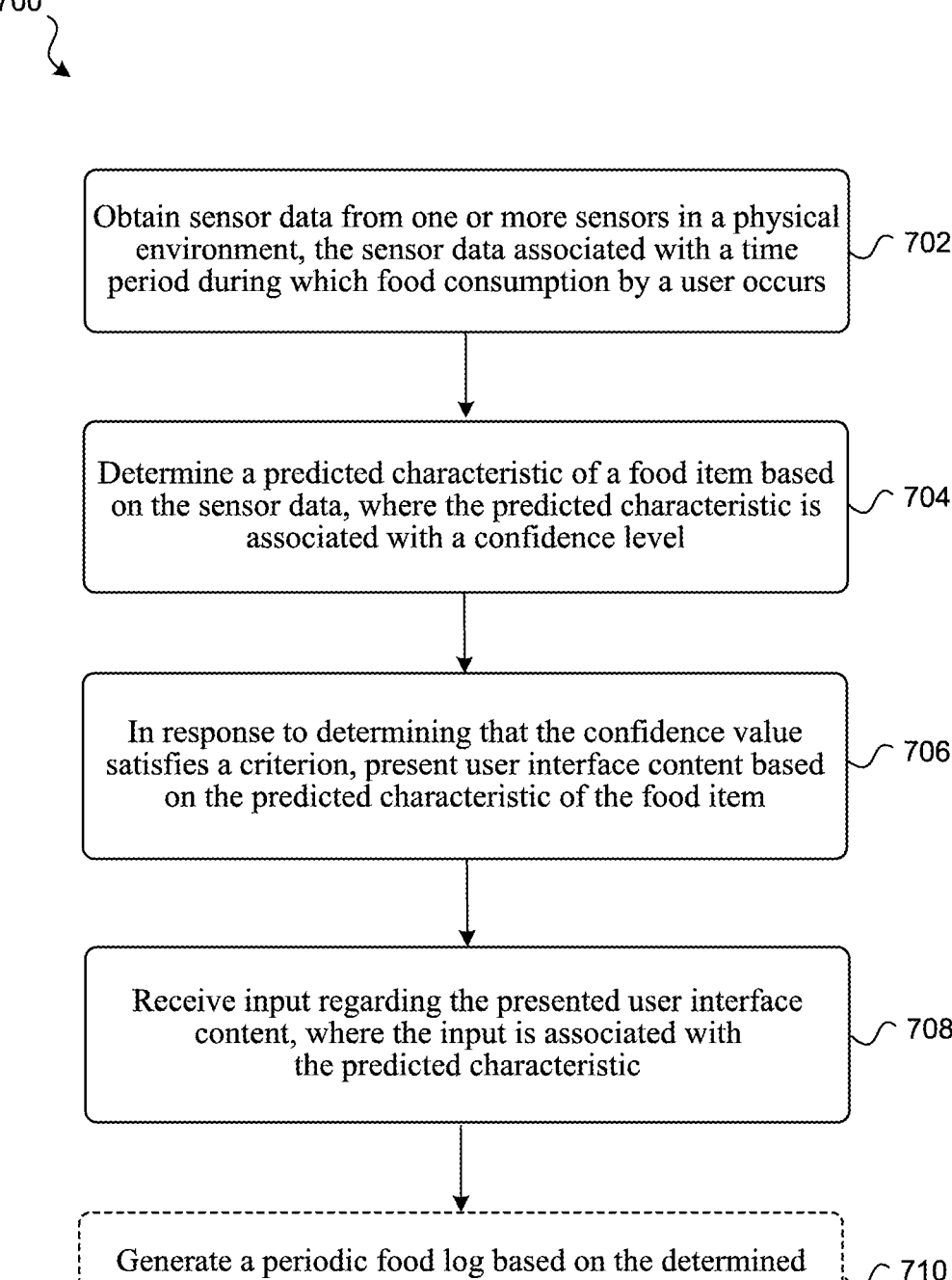

Obtain sensor data from one or more sensors in a physical environment, the sensor data associated with a time period during which food consumption by a user occurs ⌇⌐ 702

Determine a predicted characteristic of a food item based on the sensor data, where the predicted characteristic is associated with a confidence level ⌇⌐ 704

In response to determining that the confidence value satisfies a criterion, present user interface content based on the predicted characteristic of the food item ⌇⌐ 706

Receive input regarding the presented user interface content, where the input is associated with the predicted characteristic ⌇⌐ 708

Generate a periodic food log based on the determined predicted characteristic and the input ⌇⌐ 710

FIG. 7

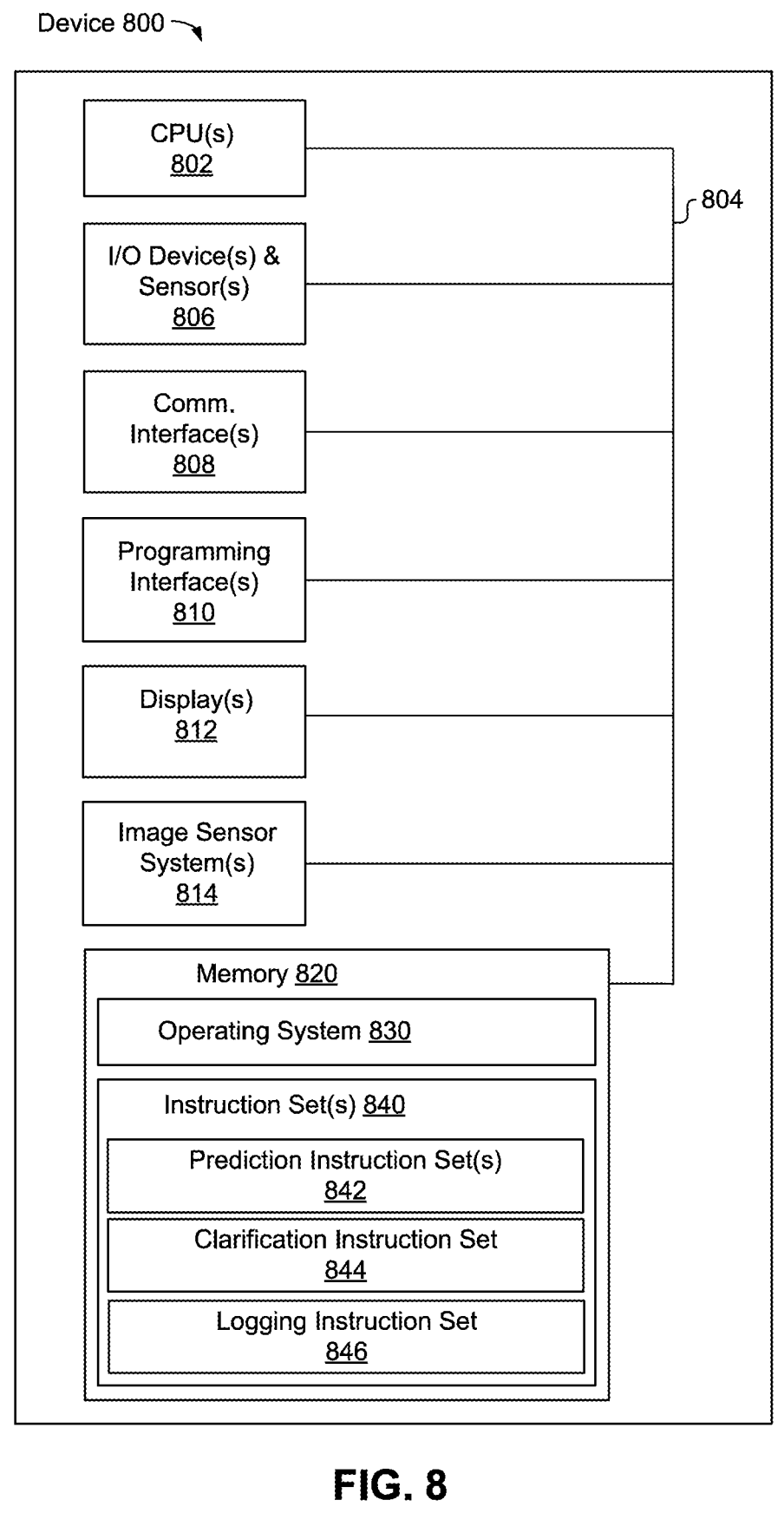

Device 800

CPU(s)
802

I/O Device(s) &
Sensor(s)
806

Comm.
Interface(s)
808

Programming
Interface(s)
810

Display(s)
812

Image Sensor
System(s)
814

804

Memory 820

Operating System 830

Instruction Set(s) 840

Prediction Instruction Set(s)
842

Clarification Instruction Set
844

Logging Instruction Set
846

FIG. 8

USER FEEDBACK DURING FOOD TRACKING

CROSS-REFERENCE TO RELATED APPLICATIONS

This application claims the benefit of U.S. Provisional Application Ser. No. 63/332,820 filed Apr. 20, 2022, which is incorporated herein in its entirety.

TECHNICAL FIELD

The present disclosure generally relates to electronic devices that use sensor data to make assessments of physical environments, including devices that use sensor data to track food characteristics.

BACKGROUND

Existing food tracking systems may be improved with respect to efficiency and accuracy.

SUMMARY

Various implementations disclosed herein use user input received approximately around the time of food consumption to confirm and/or revise food predictions, e.g., regarding type of food, volume, etc. Food characteristics may be identified for some food items with a high confidence level using sensor data, e.g., determining with 99% certainty that a food item depicted in image data is cheese pizza, determining that with 95% certainty a food volume is a single scoop of ice cream, etc. In other instances, one or more food characteristic determinations may be associated with uncertainty, e.g., determining with 60% confidence value that a given item is mashed potatoes and with 30% confidence value that the item is ice cream, determining that a food volume is a single scoop with 50% confidence value and two scoops with 45% confidence value. Implementations request user input to resolve such ambiguities and uncertainties approximately around the time of food consumption. The user feedback experience may be configured to be convenient and unobtrusive by presenting limited options in limited circumstances and using convenient and intuitive input mechanisms. As examples, such feedback may involve a user using gaze input, a voice command, or a hand gesture to quickly identify whether an uncertain item is of one type or another type, e.g., mashed potatoes or ice-cream, or whether a food volume is a single scoop or two scoops.

In some implementations, the obtrusiveness/burden of requiring live input for every food determination is avoided or minimized by only asking about some items, e.g., only asking about food items for which a characteristic is below a predefined confidence level or only asking for clarifying feedback once every 3 minutes.

Food characteristic data that is confirmed and/or revised approximately around the time of the food consumption can be used to generate food data, e.g., a meal food log, a daily food log, a weekly food log, etc., that can be presented to the user for further revisions and review at a later (non-live) time, e.g., at the end of each meal, day, week, etc. The revisions required at such time may be less than otherwise since some of the ambiguities may have been resolved previously, e.g., around the time of food consumption using the techniques presented herein.

In some implementations, a processor performs a method by executing instructions stored on a computer readable medium. The method obtains sensor data from one or more sensors in a physical environment. The sensor data is associated with a time period during which food consumption by a user occurs, e.g., during a meal, during a snack, during a period of time that a user is at a restaurant, etc. The sensor data may include image sensor data, sound sensor data, depth sensor data, location sensor data, etc.

The method determines a predicted characteristic (e.g., food type, food volume depicted, food volume consumed, etc.) of a food item based on the sensor data. The predicted characteristic is associated with a confidence value and the method, in response to determining that the confidence value satisfies a criterion, presents user interface content based on the predicted characteristic of the food item. For example, a confidence level associated with the predicted characteristic may be determined to be below a threshold confidence level, e.g., less than an 80%, 70%, 60%, etc. confidence that an item is mashed potatoes. In another example, multiple different values for a given food characteristic may be determined to each be associated with respective confidence levels that are above a threshold (e.g., the confidence level that an item is mashed potatoes and the confidence level that the item is ice cream may both be above 35%, 40%, 45%, etc.) or within a threshold amount of one another (e.g., the confidence values may be within 5%, 10%, 15%, 20% of one another).

The user interface content may be configured to implicitly or explicitly encourage a user to provide optional feedback to clarify potential uncertainty about the predicted food characteristic. For example, this may involve presenting text and/or graphics corresponding to different options (mashed potatoes or ice cream) in an extended reality (XR) view that includes depictions of the food item and that a user can interact with via gaze, voice, gesture, etc. to provide responsive input. The method may present a single option for to enable the user to confirm a food prediction. The method may present multiple options for the user to select from two or more possibilities, e.g., presenting a list of at least 2 food items based on confidence values, e.g., the top 2 likely food item types, the top 3 likely food item types, the top 4 likely food item types, etc.

The method receives input regarding the presented user interface content, where the input is associated with the predicted characteristic. In some implementations, a user interface is configured to enable a user to resolve uncertainty with respect to a food prediction using a single input or only a few inputs. In some implementations, a first user input is used to identify one of two or more food types and a second input is used to identify or associate the food item as a selected food item, e.g., identifying that the user is eating mashed potatoes and then identify which food item on the user's plate is the mashed potatoes. In other implementations, a first user input is used to identify one of two or more food types and a second input is used to identify one of two or more food volumes.

The user interface content and responsive input may occur in the time period during which food consumption occurs, e.g., during the meal, within a threshold amount of time of a particular food consumption activity such as the user putting a new food item on their plate, directly (e.g., within a few seconds) after a sensor data used in live food determination are obtained, etc. The user interface content may be presented while at least some of the associated food item is still present in the user's physical environment and/or while the food item easily recalled due to its recent presence in the user's physical environment. In some implementations, sensor data such as images of the food item are captured and retained for presentation to refresh a user's recollection regarding one or more food items.

The user interface content and/or forms of responsive input may be configured to be non-obtrusive and not inconvenient for the user, while still resolving some ambiguity so that a created food tracking record/log is more accurate than it otherwise would be. The user's experience while eating is convenient, quick, unobtrusive, efficient, and/or customized to the user's preferences for live food determination interactions, while also producing a relatively accurate record that may require no or minimal revisions at a later point in time, e.g., at the end of the meal, day, week, etc.

In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein. In accordance with some implementations, a non-transitory computer readable storage medium has stored therein instructions, which, when executed by one or more processors of a device, cause the device to perform or cause performance of any of the methods described herein. In accordance with some implementations, a device includes: one or more processors, a non-transitory memory, and means for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 7 is a flowchart illustrating a method for predicting a food characteristic in accordance with some implementations.

FIG. 8 is a block diagram of an electronic device in accordance with some implementations.

Figure 1:
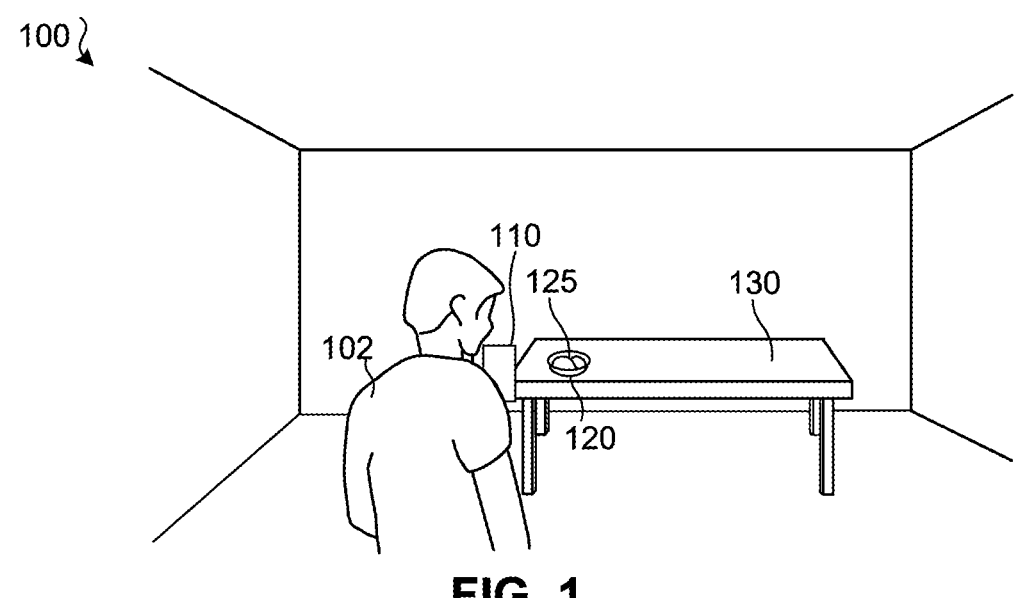
FIG. 1 illustrates a physical environment in which an electronic device is used in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

FIG. 1 illustrates a physical environment 100 in which a user 102 uses an exemplary electronic device 110. The physical environment 100 in this example is room that includes a table 130. The electronic device 110 includes one or more cameras, microphones, vibration sensors, depth sensors, motion sensors, location sensors, or other sensors that can be used to capture information about and evaluate the physical environment 100 and the objects within it, as well as information about the user 102. The information about the physical environment 100 or user 102 may be used to assess the physical environment 100 (e.g., tracking food, the user's consumption of food, etc.), identify conditions (e.g., user activity or environment characteristics) and/or to provide visual and audio content.

In FIG. 1, the table surface of the table 130 has bowl 120 containing a food item 125. The user is in front of the bowl 120, e.g., that bowl 120 is within an eating area defined by the device 110 for the user 102. An eating area may be defined in various ways for example using various criteria, e.g., based on a threshold distance in front of the user (e.g., within arm's reach), based on identifying an area that is closer to the user than another user, based on user preferences, based on user input identifying the eating area, based on user interactions (e.g., detecting the user interacting within an area), etc.

Various implementations disclosed herein use user input received (e.g., detected based on sensor data) by device 110 approximately around the time of food consumption to confirm and/or revise food predictions, e.g., regarding type of food, volume, etc. Sensor data may be used to determine a predicted food characteristic (e.g., a type of food (e.g., pork or chicken), a variant or variable attribute (e.g., diet, zero, regular, sugar free, caffeine free, lactose free, fat free, whole milk-based, etc.) of a food item, a volume or weight of the food item, a volume or weight of the food item that has been consumed, etc.).

Predicted food characteristics of at least some food items may be confirmed and/or revised based on user input. For example, in FIG. 1, the device 110 may determine with a first confidence level (e.g., 45%) that the food item 125 is mashed potatoes and a second confidence level (e.g., 45%) that the food item 125 is ice cream. The device 110 may present content that requests (explicitly or implicitly) that the user 102 can optionally do something to provide clarification or otherwise resolve the uncertainty approximately around the time of food consumption. For example, a user may effectuate a selection by fixing his or her gaze on one of multiple selectable options. In some implementations, gaze alone (e.g., without hand, voice, or other type of input) is enough to effectuate a selection. In other implementations, pinch, pointing, other hand gestures, voice commands, body motions, or any other type of input may be additionally or alternatively used. In some implementations, the required input my be achieved without requiring the user to put down a utensil (with or without a food item on it) or a food item itself.

Figure 2A:
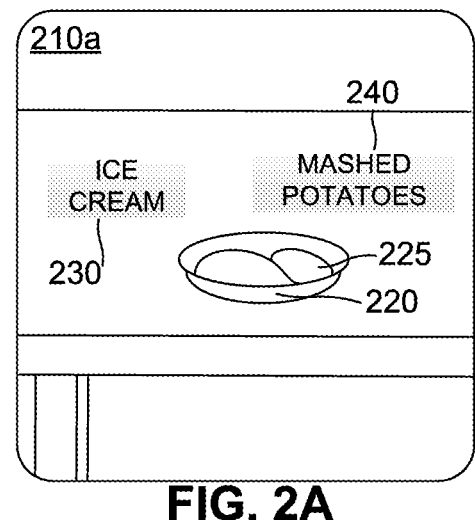
FIGS. 2A and 2B illustrate examples of user interface content and responsive input in an extended reality experience that is provided based on the physical environment of FIG. 1, in accordance with some implementations.
Figure 2B:
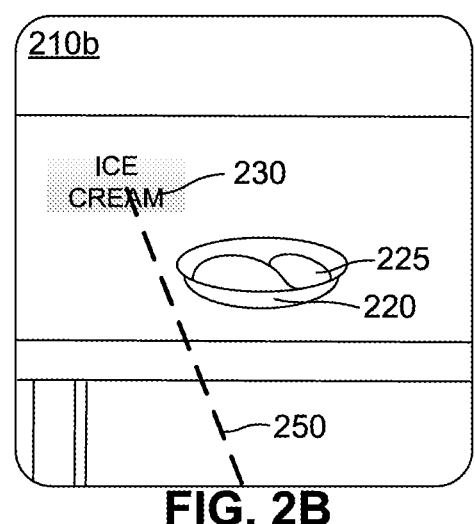

FIGS. 2A and 2B provide views 210a-b that illustrate examples of provided content and responsive input that clarifies or resolves food characteristics during a live extended reality (XR) experience provided based on the physical environment of FIG. 1. The views 210a-b include depiction 220 of the bowl 120 and depiction 225 of the food item 125. In this example, during a meal or other period of time during which the user 102 consumes one or more food items (e.g., food item 125) in the physical environment 100, the device 110 provides virtual content 230, 240 and receives input 250 to clarify or resolve uncertainties regarding a food type food characteristic determination. In this example, device 110 has determined with a first confidence level (e.g., 45%) that the food item 125 is mashed potatoes and a second confidence level (e.g., 45%) that the food item 125 is ice cream. Based on determining a determination that there is a sufficient amount of uncertainty and/or that the current circumstances of the XR experience are suitable for clarifying user input, the device 110 presents a first virtual content item 230 showing floating text "ICE CREAM" and a second virtual content item 240 showing floating text "MASHED POTATOES." In this example, the user responds to this implicit request for clarification by gazing at the correct item type. The device 110 identifies this input, e.g., identifying gaze direction 250 and that the gaze in that gaze direction 250 lasted for at least a threshold amount of time. The device 110 uses this recognized input to resolve the uncertainty, e.g., logging the food item 125 with food item type "ICE CREAM" in a daily food log for the user 102.

In the example of FIGS. 2A-2B, the device 110 determines to present the virtual content 230, 240 based on a determination that there is a sufficient amount of uncertainty, e.g., based on one or more confidence values. Various criteria may be used to assess whether a determined amount of uncertainty is sufficient. For example, a sufficient amount of uncertainty may be determined to exist is circumstances in which no single prediction has a confidence value that exceeds a threshold value, e.g., 50%, 60%, 70%, 80%, etc. In another example, a sufficient amount of uncertainty may be determined to exist in circumstances in which multiple, alternative predictions have confidence values that are above a given threshold, e.g., above 30%, 35%, 40%, 45%, etc. In another example, a sufficient amount of uncertainty may be determined to exist in circumstances in which the top two predictions have confidence values that are sufficiently close to one another, e.g., within 3%, 5%, 10%, 20%, etc. of one another.

In the example of FIGS. 2A-2B, the device 110 determines to present the virtual content 230, 240 based on a determination that the current circumstances of the XR experience are suitable for clarifying user input. For example, the device 110 may limit the number and/or frequency of clarification requests, e.g., not more than 4 requests per hour, no more than 3 requests during a meal, no more than 1 request every 2 minutes, etc. In another example, the device 110 may limit the presentation of clarification requests based on what the user is doing, the presence of other persons, the type of environment (e.g., at home or in a restaurant), whether the user responded or not to a prior request, etc.

Figure 3A:
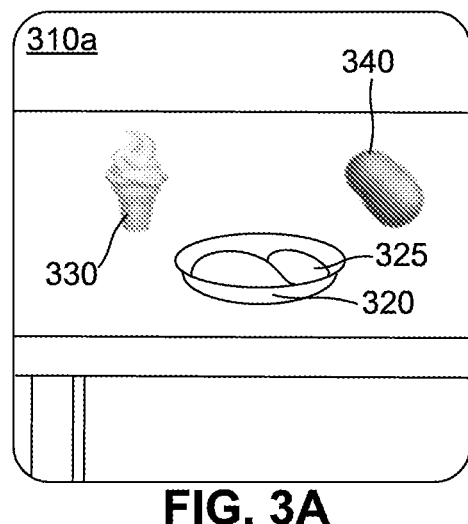
FIGS. 3A and 3B illustrate additional examples of user interface content and responsive input in an extended reality experience provided based on the physical environment of FIG. 1, in accordance with some implementations.
Figure 3B:
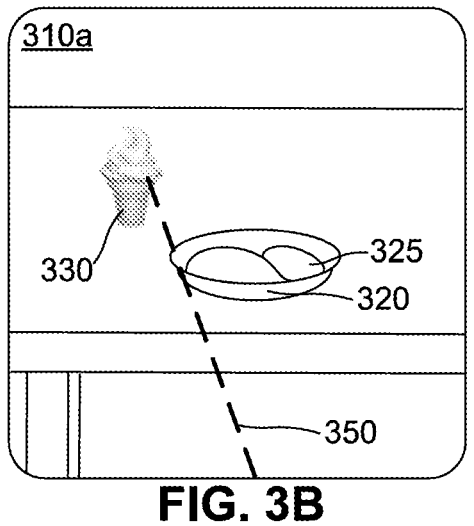

FIGS. 3A and 3B illustrate views 310a-b that provide additional examples of provided content and responsive input in an extended reality (XR) experience provided based on the physical environment of FIG. 1. The views 310a-b include depiction 320 of the bowl 120 and depiction 325 of the food item 125. In this example, during the meal or other period of time during which the user 102 consumes one or more food items (e.g., food item 125) in the physical environment 100, the device 110 provides virtual content 330, 340 and receives input 350 to clarify or resolve uncertainties regarding a food type food characteristic determination. In this example, device 110 has determined with a first confidence level (e.g., 38%) that the food item 125 is mashed potatoes and a second confidence level (e.g., 60%) that the food item 125 is ice cream. Based on the determination that there is a sufficient amount of uncertainty and/or that the current circumstances of the XR experience are suitable for clarifying user input, the device 110 presents a first virtual content item 330 showing a 3D graphical ice cream cone and a second virtual content item 340 showing a 3D graphical potato. In this example, the user responds to this implicit request for clarification by gazing at the representation of the appropriate item type. The device 110 identifies this input, e.g., identifying gaze direction 350 and that the gaze in that gaze direction 350 lasted for at least a threshold amount of time. The device 110 uses this recognized input to resolve the uncertainty, e.g., logging the food item 125 with food item type "ICE CREAM" in a daily food log for the user 102.

In the example of FIGS. 3A-3B, the virtual content 310, 320 provides representations that do not exactly correspond to the corresponding item type. Virtual content 330 is an ice cream cone (rather than a couple scoops of ice cream) and virtual content 340 is a whole potato (rather than a couple piles of mashed potatoes). In this example, the user is able to clarify the ambiguity simply by selecting the virtual content that is more like the food item, e.g., an ice cream cone is more like ice cream scoops in a bowl than a potato is like ice cream scoops in a bowl. The device 110 may include representations that are easily recognizable for food items to facilitate easier understanding and selection by the user 102. The representations may be configured based on user preferences, e.g., the user may provide a preference for text-based clarification requests, graphical depiction-based clarification requests, or combined text-graphic clarification requests.

In the examples of FIGS. 2A-2B and 3A-3B, the virtual content 230, 240, 330, 340 are positioned to facilitate easy understanding and input by the user. For example, this may involve determining a 3D position of a food item, nearby items, and/or the user's relative position and selecting positions at which to display the virtual content 230, 240, 330, 340 that indicate an association with a particular food item, e.g., presenting the virtual content 230, 240, 330, 340 within a predetermined 3D distance of the food item and/or within a predetermined 2D distance within a view (e.g., within views 210, 220, 310, 330). The virtual content 230, 240, 330, 340 may similarly be positioned and/or sized to avoid obscuring the user's view of real or virtual content with which the user is interacting or near, e.g., of other food items, other people, etc.

In some implementations, the virtual content 230, 240, 330, 340 changes over time to indicate that the user should respond (if at all) within a period of time. For example, the virtual content 230, 240, 330, 340 may gradually fade and/or shrink over a period of a few seconds and then disappear. The virtual content 230, 240, 330, 340 may be changed and/or provided for limited durations to ensure that the user experience is not cluttered, burdened, or otherwise degraded by unwanted requests for clarifications regarding food characteristics. In some implementations, user preferences are used to adjust the frequency, number of, size, persistence, or other attributes of the virtual content that is provided to explicitly or implicitly request user clarification of food characteristic predictions. If a user does not respond to one or more clarification requests, the system may discontinue future requests during the meal or wait a predetermined amount of time before making a subsequent request.

Figure 4:
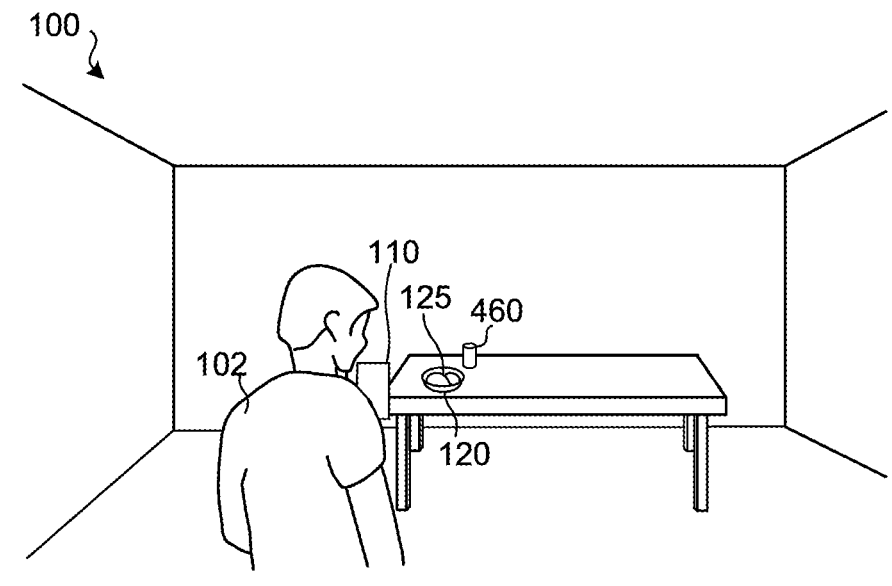
FIG. 4 illustrates the physical environment of FIG. 1 with an additional food item added, in accordance with some implementations.

FIG. 4 illustrates the physical environment of FIG. 1 with an additional food item 460 added. In some implementations, the device 110 detects that a new food item has been added (e.g., to physical environment 100 or the user's eating area) and triggers automatic food detection and/or related sensor data capture accordingly. For example, a new food item may be detected based on differences in image data, based on motion data, based on sound data, etc.

Figure 5A:
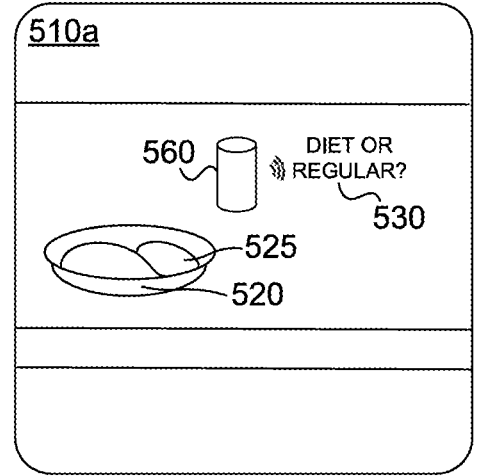
FIGS. 5A and 5B illustrate examples of user interface content and responsive input in an extended reality experience provided based on the physical environment of FIG. 4, in accordance with some implementations.
Figure 5B:
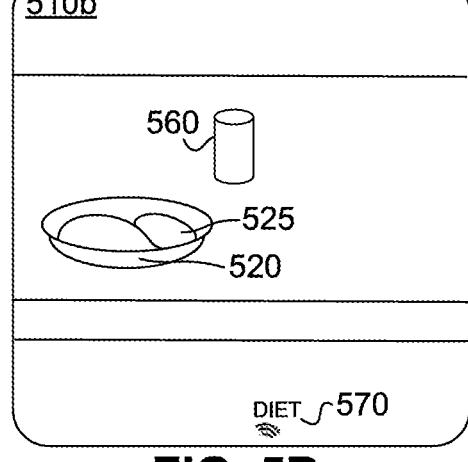

FIGS. 5A and 5B illustrate views 510a-b that provide examples of provided content and responsive input in an extended reality (XR) experience provided based on the physical environment of FIG. 4. The views 510a-b include depiction 520 of the bowl 120, depiction 525 of the food item 125, and depiction 560 of the food item 460. In this example, during a meal or other period of time during which the user 102 consumes one or more food items (e.g., food items 125, 460) in the physical environment 100, the device 110 provides virtual content 530 and receives input 570 to clarify or resolve uncertainties regarding a food characteristic determination. In this example, device 110 is uncertain whether the food item 560 includes diet soda or regular soda. Based on a determination that there is a sufficient amount of uncertainty and/or that the current circumstances of the XR experience are suitable for clarifying user input, the device 110 presents a first virtual content item 530-a spatialized audio sound positioned on or near the representation 560 of the food item 460 with the audible words "DIET OR REGULAR?" In this example, the user responds to this implicit request for clarification with input 570 by speaking the word "DIET". The device 110 identifies this input, e.g., using speak recognition on a captured audio signal from a microphone. The device 110 uses this recognized input to resolve the uncertainty, e.g., logging the food item 460 with food item attribute "DIET" in a daily food log for the user 102.

Figure 6A:
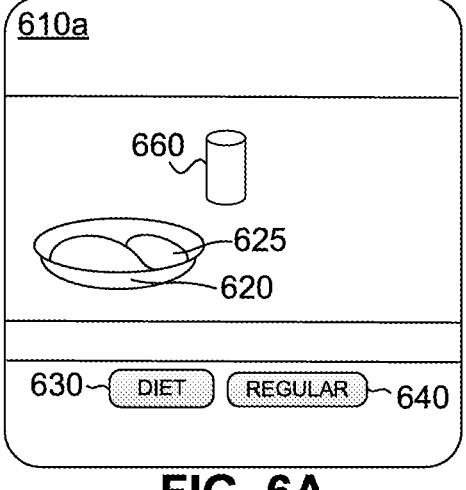
FIGS. 6A and 6B illustrate additional examples of user interface content and responsive input in an extended reality experience provided based on the physical environment of FIG. 4, in accordance with some implementations.
Figure 6B:
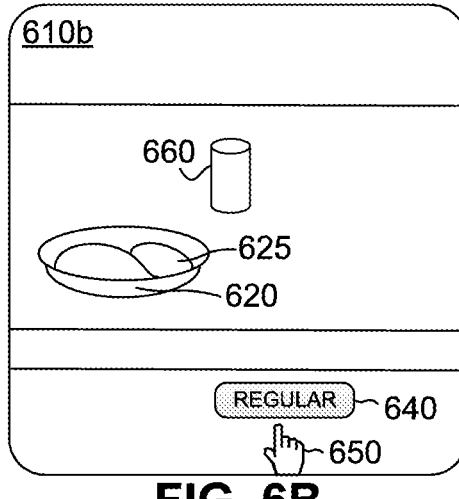

FIGS. 6A and 6B illustrate views 610a-b that provide additional examples of provided content and responsive input in an extended reality (XR) experience provided based on the physical environment of FIG. 4. The views 610a-b include depiction 620 of the bowl 120, depiction 625 of the food item 125, and depiction 660 of the food item 460. In this example, during the meal or other period of time during which the user 102 consumes one or more food items (e.g., food items 125, 460) in the physical environment 100, the device 110 provides virtual content 630, 640 and receives input 650 to clarify or resolve uncertainties regarding a food characteristic determination. In this example, device 110 is uncertain whether the food item 460 is diet or regular soda. Based on a determination that there is a sufficient amount of uncertainty and/or that the current circumstances of the XR experience are suitable for clarifying user input, the device 110 presents a first virtual content item 630 showing virtual content corresponding to a DIET option and virtual content item 640 corresponding to a REGULAR option. In this example, the user responds to this implicit request for clarification by making a hand gesture (e.g., pointing at) at the option corresponding to the appropriate attribute. The device 110 identifies this input, e.g., identifying the gesture based on image or other sensor data. The device 110 uses this recognized input to resolve the uncertainty, e.g., logging the food item 460 with food item attribute "REGULAR" in a daily food log for the user 102.

FIG. 7 is a flowchart illustrating a method 700 for method for predicting a food characteristic. In some implementations, a device such as electronic device 110 performs method 700. In some implementations, method 700 is performed on a mobile device, desktop, laptop, HMD, or server device. The method 700 is performed by processing logic, including hardware, firmware, software, or a combination thereof. In some implementations, the method 700 is performed on a processor executing code stored in a non-transitory computer-readable medium (e.g., a memory).

At block 702, the method 700 obtains sensor data from one or more sensors in a physical environment. The sensor data may be associated with a time period during which food consumption by a user occurs, e.g., during a meal, snack, cocktail party, etc. The sensor data may include image data, depth data, sound data, motion data, location data, etc.

At block 704, the method 700 determines a predicted characteristic (e.g., type, volume/amount present/consumed, etc.) of a food item based on the sensor data, where the predicted characteristic is associated with a confidence level. For example, neural network or other machine learning model may input images and/or other sensor data and produce food predictions and corresponding confidence levels. Such confidence values may be compared with thresholds and/or other criteria to identify appropriate circumstances in which to request food prediction clarifications. The method 700 may determine that the predicted characteristic is associated with uncertainty based on a determination that a confidence level of the predicted characteristic is below a threshold. The method 700 may determine that the predicted characteristic is associated with uncertainty by determining that a food type could be either a first food type or a second food type based on the sensor data. The uncertainty may be based on a context of the physical environment determined based the sensor data. For example, determinations made in at a location having a fixed food menu may be associated with less uncertainty that determinations in environments with less limited food availability.

At block 706, the method 700, in response to determining that the confidence value satisfies a criterion, presents user interface content based on the predicted characteristic of the food item. For example, a confidence level associated with the predicted characteristic may be determined to be below a threshold confidence level, e.g., less than an 80%, 70%, 60%, etc. confidence that an item is mashed potatoes. In another example, multiple different values for a given food characteristic may be determined to each be associated with respective confidence levels that are above a threshold (e.g., the confidence level that an item is mashed potatoes and the confidence level that the item is ice cream may both be above 35%, 40%, 45%, etc.) or within a threshold amount of one another (e.g., the confidence values may be within 5%, 10%, 15%, 20% of one another).

Presenting the user interface content may involve presenting text, graphics, and/or sounds corresponding to different options (e.g., mashed potatoes or ice cream) in an XR view that a user can gaze at to choose. FIGS. 2A, 3A, 5A, and 6A provide examples of presenting user interface content based on predicted characteristics of food items.

At block 708, the method 700 receives input regarding the presented user interface content, wherein the input is associated with the predicted characteristic. FIGS. 2B, 3B, 5B, and 6B provide examples of receiving input regarding predicted characteristics of food items.

The user interface content and/or input may occur in the time period during of food consumption, e.g., during the meal, within a threshold amount of time of a food consumption activity, directly after each live food determination is made, etc. The user interface content is presented within a threshold amount of time of a food consumption activity, e.g., within 5 seconds of a new food item being added to the user's plate.

The user interface content may include graphical, text, and/or audio content corresponding to two or more options presented in an extended reality view the method 700 may interpret the input (e.g., gaze, vocal utterances, spoken sounds, movements, etc.) to select an option of the two or more options. The input may be a gaze direction, voice command, movement of a device (e.g., ring), etc. corresponding to a mashed potatoes option.

The user interface content and/or input may be configured to be non-obtrusive and not inconvenient while still resolving some ambiguity so that, at the end of the day (or other time period), the food tracking record is more accurate than it otherwise would be. The user's experience during the day is not excessively burdened, while also producing a relatively accurate record that requires minimal revisions.

Sensor data (e.g., images) may be captured by a sensor on a device worn by the user and oriented to capture data corresponding to the environment in front of the user, e.g., capturing images of a top surface of a table in front of the user including the user's plate(s), etc. The sensor data may be obtained by capturing images via an outward facing camera of a top surface of a table in front of the user. The sensor data may include images captured and/or processed at a rate that is less than one image per twenty seconds. Audio, motion, vibration, location, and/or depth sensor data may be captured. The rate of sensor data capture and/or processing may be adapted based on a determination a context, e.g., whether the user is eating, the user's rate of consumption, the type of food, how many other people are nearby, etc.

In some implementations, a head mounted device comprising one or more front-facing sensors (e.g., a front facing image sensor, a front facing depth sensor, etc.) is used to perform method 700.

In some implementations, the device that provides food consumption tracking also provides views of an extended reality (XR) environment. Such an XR environment may include views of a 3D environment that is generated based on camera images or depth camera images of the physical environment 100 as well as a representation of user 102 based on camera images or depth camera images of the user 102. Such an XR environment may include virtual content that is overlain on views of the physical environment 100 or that is positioned at 3D locations relative to a 3D coordinate system associated with the XR environment, which may correspond to a 3D coordinate system of the physical environment 100. For example, virtual content may be displayed based on food tracking determinations, e.g., showing indicators when a new food item has been detected within a user's eating area, showing indicators tracking the calories, macro-nutrients, etc., that are in the food added to a user's eating area and/or consumed by the user 102.

A physical environment refers to a physical world that people can sense or interact with without aid of electronic systems. The physical environment may include physical features such as a physical surface or a physical object. For example, the physical environment corresponds to a physical park that includes physical trees, physical buildings, and physical people. People can directly sense or interact with the physical environment, such as through sight, touch, hearing, taste, and smell. In contrast, an extended reality (XR) environment refers to a wholly or partially simulated environment that people sense or interact with via an electronic device. For example, the XR environment may include augmented reality (AR) content, mixed reality (MR) content, virtual reality (VR) content, or the like. With an XR system, a subset of a person's physical motions, or representations thereof, are tracked, and, in response, one or more characteristics of one or more virtual objects simulated in the XR environment are adjusted in a manner that comports with at least one law of physics. As one example, the XR system may detect rotational head movement and, in response, adjust graphical content and an acoustic field presented to the person in a manner similar to how such views and sounds would change in a physical environment. As another example, the XR system may detect rotational or translational movement of the electronic device presenting the XR environment (e.g., a mobile phone, a tablet, a laptop, or the like) and, in response, adjust graphical content and an acoustic field presented to the person in a manner similar to how such views and sounds would change in a physical environment. In some situations (e.g., for accessibility reasons), adjustments to characteristic(s) of graphical content in an XR environment may be made in response to representations of physical motions (e.g., vocal commands).

There are many different types of electronic systems that enable a person to sense or interact with various XR environments. Examples include head mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mountable system may have one or more speaker(s) and an integrated opaque display. Alternatively, a head mountable system may be configured to accept an external opaque display (e.g., a smartphone). The head mountable system may incorporate one or more imaging sensors to capture images or video of the physical environment, or one or more microphones to capture audio of the physical environment. Rather than an opaque display, a head mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In some implementations, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

FIG. 8 is a block diagram of electronic device 800. Device 800 illustrates an exemplary device configuration for electronic device 810. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 800 includes one or more processing units 802 (e.g., microprocessors, ASICs, FPGAs, GPUs, CPUs, processing cores, or the like), one or more input/output (I/O) devices and sensors 806, one or more communication interfaces 808 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, or the like type interface), one or more programming (e.g., I/O) interfaces 810, one or more output device(s) 812, one or more interior or exterior facing image sensor systems 814, a memory 820, and one or more communication buses 804 for interconnecting these and various other components.

In some implementations, the one or more communication buses 804 include circuitry that interconnects and controls communications between system components. In some implementations, the one or more I/O devices and sensors 806 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), or the like.

In some implementations, the one or more output device(s) 812 include one or more displays configured to present a view of a 3D environment to the user. In some implementations, the one or more displays 812 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electromechanical system (MEMS), or the like display types. In some implementations, the one or more displays correspond to diffractive, reflective, polarized, holographic, etc. waveguide displays. In one example, the device 800 includes a single display. In another example, the device 500 includes a display for each eye of the user.

In some implementations, the one or more output device(s) 812 include one or more audio producing devices. In some implementations, the one or more output device(s) 812 include one or more speakers, surround sound speakers, speaker-arrays, or headphones that are used to produce spatialized sound, e.g., 3D audio effects. Such devices may virtually place sound sources in a 3D environment, including behind, above, or below one or more listeners. Generating spatialized sound may involve transforming sound waves (e.g., using head-related transfer function (HRTF), reverberation, or cancellation techniques) to mimic natural soundwaves (including reflections from walls and floors), which emanate from one or more points in a 3D environment. Spatialized sound may trick the listener's brain into interpreting sounds as if the sounds occurred at the point(s) in the 3D environment (e.g., from one or more particular sound sources) even though the actual sounds may be produced by speakers in other locations. The one or more output device(s) 812 may additionally or alternatively be configured to generate haptics.

In some implementations, the one or more image sensor systems 814 are configured to obtain image data that corresponds to at least a portion of a physical environment. For example, the one or more image sensor systems 814 may include one or more RGB cameras (e.g., with a complimentary metal-oxide-semiconductor (CMOS) image sensor or a charge-coupled device (CCD) image sensor), monochrome cameras, IR cameras, depth cameras, event-based cameras, or the like. In various implementations, the one or more image sensor systems 814 further include illumination sources that emit light, such as a flash. In various implementations, the one or more image sensor systems 814 further include an on-camera image signal processor (ISP) configured to execute a plurality of processing operations on the image data.

The memory 820 includes high-speed random-access memory, such as DRAM, SRAM, DDR RAM, or other random-access solid-state memory devices. In some implementations, the memory 820 includes non-volatile memory, such as one or more magnetic disk storage devices, optical disk storage devices, flash memory devices, or other non-volatile solid-state storage devices. The memory 820 optionally includes one or more storage devices remotely located from the one or more processing units 802. The memory 820 comprises a non-transitory computer readable storage medium.

In some implementations, the memory 820 or the non-transitory computer readable storage medium of the memory 820 stores an optional operating system 830 and one or more instruction set(s) 840. The operating system 830 includes procedures for handling various basic system services and for performing hardware dependent tasks. In some implementations, the instruction set(s) 840 include executable software defined by binary information stored in the form of electrical charge. In some implementations, the instruction set(s) 840 are software that is executable by the one or more processing units 802 to carry out one or more of the techniques described herein.

The instruction set(s) 840 include prediction instruction set(s) 542 configured to, upon execution, predict food characteristics using sensor data as described herein. The instruction set(s) 840 further include a clarification instruction set 844 configured to, upon execution, provide content and receive input to clarify food predictions as described herein. The instruction set(s) 840 further include a logging instruction set 844 configured to, upon execution, generate a food log and present a user interface for viewing and/or editing a food log as described herein. The instruction set(s) 840 may be embodied as a single software executable or multiple software executables.

Although the instruction set(s) 840 are shown as residing on a single device, it should be understood that in other implementations, any combination of the elements may be located in separate computing devices. Moreover, the figure is intended more as functional description of the various features which are present in a particular implementation as opposed to a structural schematic of the implementations described herein. As recognized by those of ordinary skill in the art, items shown separately could be combined and some items could be separated. The actual number of instructions sets and how features are allocated among them may vary from one implementation to another and may depend in part on the particular combination of hardware, software, or firmware chosen for a particular implementation.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

As described above, one aspect of the present technology is the gathering and use of sensor data that may include user data to improve a user's experience of an electronic device. The present disclosure contemplates that in some instances, this gathered data may include personal information data that uniquely identifies a specific person or can be used to identify interests, traits, or tendencies of a specific person. Such personal information data can include movement data, physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to improve the content viewing experience. Accordingly, use of such personal information data may enable calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information or physiological data will comply with well-established privacy policies or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying or personal information about the user, such as a legal name, username, time and location data, or the like). In this way, other users, hackers, or third parties cannot determine the identity of the user associated with the stored data. In some implementations, a user may access their stored data from a user device that is different than the one used to upload the stored data. In these instances, the user may be required to provide login credentials to access their stored data.

Numerous specific details are set forth herein to provide a thorough understanding of the claimed subject matter. However, those skilled in the art will understand that the claimed subject matter may be practiced without these specific details. In other instances, methods apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:
at an electronic device having a processor:
    obtaining sensor data from one or more sensors in a physical environment, the sensor data associated with a time period during which food consumption by a user occurs;
    determining a predicted characteristic of a food item based on the sensor data, wherein the predicted characteristic is associated with a confidence value corresponding to confidence that the food item has the predicted characteristic;
    in response to determining that the confidence value corresponding to confidence that the food item has the predicted characteristic satisfies a criterion, presenting user interface content based on the predicted characteristic of the food item; and
    receiving input regarding the presented user interface content, wherein the input is associated with the predicted characteristic.

2. The method of claim 1, wherein the user interface content is presented and the input is received during the time period during which the food consumption occurs.

3. The method of claim 1, wherein the user interface content is presented and the input is received during a meal during which the food consumption by the user occurs.

4. The method of claim 1, wherein the user interface content is presented within a threshold amount of time of a food consumption activity.

5. The method of claim 1, wherein determining that the confidence value satisfies the criterion is based on determining that the confidence level of the predicted characteristic is below a threshold.

6. The method of claim 1, wherein determining that the confidence value satisfies the criterion is based on determining that a food type could be either a first food type or a second food type based on the sensor data.

7. The method of claim 1, wherein the user interface content comprises graphical content corresponding to two or more options presented in an extended reality view.

8. The method of claim 7 further comprising interpreting the input to select an option of the two or more options.

9. The method of claim 1, wherein the input is based on determining a gaze direction of the user.

10. The method of claim 1, wherein the input is based on a vocal utterance of the user.

11. The method of claim 1, wherein the input is based on a movement of the user or a second electronic device operated by the user.

12. The method of claim 1, wherein determining that the confidence value satisfies the criterion is based on a context of the physical environment determined based the sensor data.

13. A system comprising:
a non-transitory computer-readable storage medium; and
one or more processors coupled to the non-transitory computer-readable storage medium, wherein the non-transitory computer-readable storage medium comprises program instructions that, when executed on the one or more processors, cause the system to perform operations comprising:
    obtaining sensor data from one or more sensors in a physical environment, the sensor data associated with a time period during which food consumption by a user occurs;
    determining a predicted characteristic of a food item based on the sensor data, wherein the predicted characteristic is associated with a confidence value corresponding to confidence that the food item has the predicted characteristic;
    in response to determining that the confidence value corresponding to confidence that the food item has the predicted characteristic satisfies a criterion, presenting user interface content based on the predicted characteristic of the food item; and receiving input regarding the presented user interface content, wherein the input is associated with the predicted characteristic.

14. The system of claim 13, wherein the user interface content is presented and the input is received during the time period during which the food consumption occurs.

15. The system of claim 13, wherein the user interface content is presented and the input is received during a meal during which the food consumption by the user occurs.

16. The system of claim 13, wherein the user interface content is presented within a threshold amount of time of a food consumption activity.

17. The system of claim 13, wherein determining that the confidence value satisfies the criterion is based on determining that a confidence level of the predicted characteristic is below a threshold.

18. The system of claim 13, wherein determining that the confidence value satisfies the criterion is based on determining that a food type could be either a first food type or a second food type based on the sensor data.

19. The system of claim 13, wherein the user interface content comprises graphical content corresponding to two or more options presented in an extended reality view.

20. A non-transitory computer-readable storage medium storing program instructions executable via one or more processors to perform operations comprising:

obtaining sensor data from one or more sensors in a physical environment, the sensor data associated with a time period during which food consumption by a user occurs;

determining a predicted characteristic of a food item based on the sensor data, wherein the predicted characteristic is associated with a confidence value corresponding to confidence that the food item has the predicted characteristic;

in response to determining that the confidence value corresponding to confidence that the food item has the predicted characteristic satisfies a criterion, presenting user interface content based on the predicted characteristic of the food item; and receiving input regarding the presented user interface content, wherein the input is associated with the predicted characteristic.

\* \* \* \* \*